United States Patent
Tanimoto et al.

(10) Patent No.: US 9,775,924 B2
(45) Date of Patent: Oct. 3, 2017

(54) DECONTAMINATION PROCESS DEVICE AND DECONTAMINATION PROCESS METHOD

(71) Applicant: SHIBUYA KOGYO CO., LTD., Kanazawa-shi, Ishikawa (JP)

(72) Inventors: Kazuhito Tanimoto, Kanazawa (JP); Tomoo Matsuoka, Kanazawa (JP)

(73) Assignee: SHIBUYA KOGYO CO., LTD., Kanazawa-shi, Ishikawa (JP)

( * ) Notice: Subject to any disclaimer, the term of this patent is extended or adjusted under 35 U.S.C. 154(b) by 162 days.

(21) Appl. No.: 14/579,289

(22) Filed: Dec. 22, 2014

(65) Prior Publication Data

US 2015/0182651 A1    Jul. 2, 2015

(30) Foreign Application Priority Data

Dec. 26, 2013    (JP) .................................. 2013-268273

(51) Int. Cl.
*A61L 2/20* (2006.01)

(52) U.S. Cl.
CPC ........... *A61L 2/208* (2013.01); *A61L 2202/14* (2013.01)

(58) Field of Classification Search
CPC ....................................................... A61L 2/208
See application file for complete search history.

(56) References Cited

U.S. PATENT DOCUMENTS

2006/0008378 A1    1/2006  Imai et al.

FOREIGN PATENT DOCUMENTS

JP            4380411 B2   11/2005
JP            5163882 B2   12/2009

*Primary Examiner* — Donald Spamer
(74) *Attorney, Agent, or Firm* — Muncy, Geissler, Olds & Lowe, P.C.

(57) ABSTRACT

A decontamination process device includes a chamber that contains a decontamination target, a heating device that generates decontamination vapor, an air sending part that sends the decontamination vapor into the chamber, a ventilation system that ventilates the chamber, a controller that controls operations of the decontamination process device. The controller performs a supply process that supplies the decontamination vapor into the chamber and an elimination process that eliminates a decontamination component after the supply process. The ventilation system adjusts an ventilation amount and the controller is set to repeat the supply processes at multiple times, and to perform a dry process between the repeated supply processes and to maintain the chamber at a positive pressure during the dry process.

4 Claims, 2 Drawing Sheets

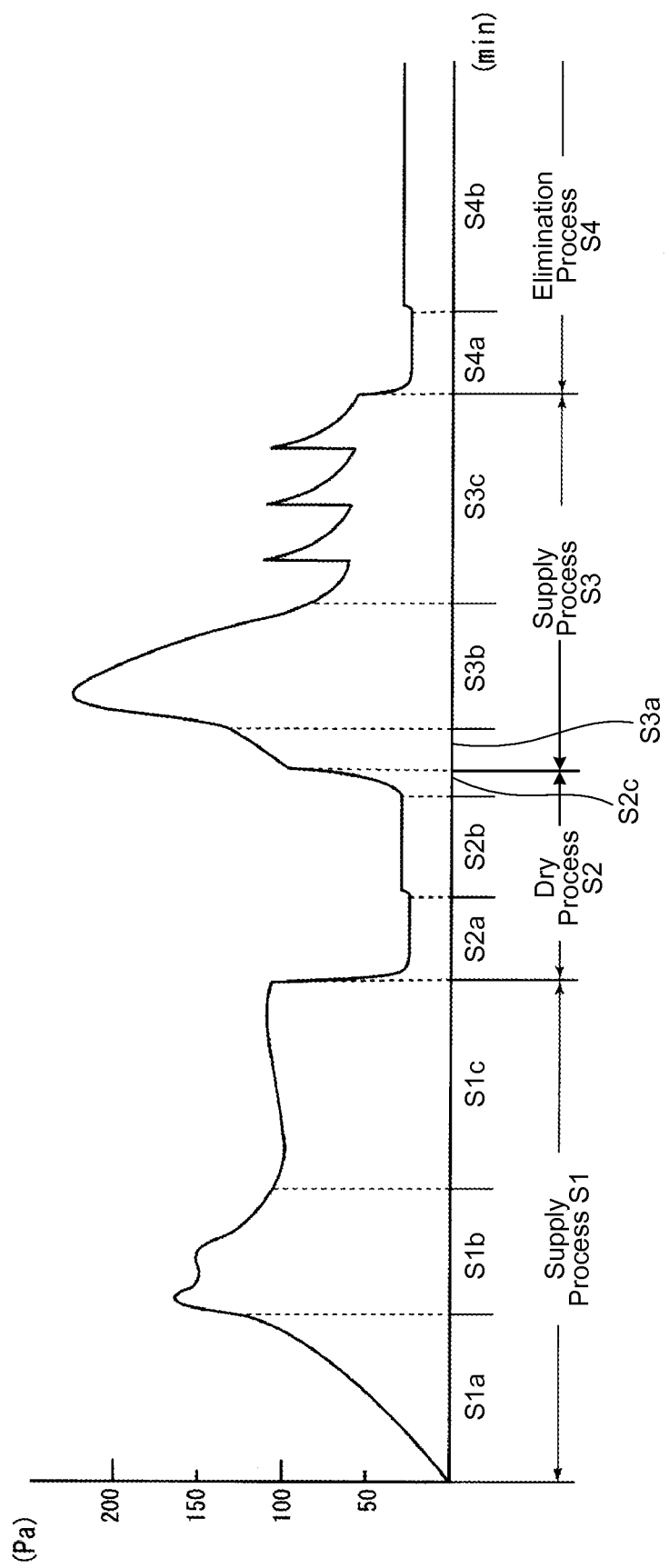

DECONTAMINATION PROCESS DEVICE AND DECONTAMINATION PROCESS METHOD

CROSS REFERENCE

The present application is related to, claims priority from and incorporates by reference Japanese Patent Application No. 2013-268273, filed on Dec. 26, 2013.

TECHNICAL FIELD

The invention relates to a decontamination process device and decontamination process method, specifically to a process device and process method including a supply process in which a predetermined amount of decontamination vapor is supplied into a chamber and an elimination process in which a contaminant, which is a target of the decontamination, in the chamber is eliminated.

BACKGROUND

Conventionally, a decontamination process device for decontaminating a decontamination target is known, in which a chamber that contains the decontamination target, a heating device that vaporizes a decontamination agent, an air sending part that sends a decontamination vapor (or vapor made from the decontamination agent by vaporizing the agent) that was vaporized into the chamber, a ventilation system that ventilates the chamber, and a controller that controls those operations are assembled (see patent document 1).

According to a decontamination process method by the decontamination process device, a supply process and an elimination process are performed, the supply process supplying a predetermined amount of the decontamination vapor into the chamber by operating the heating device and the air sending part and the elimination process for eliminating decontamination targets in the chamber by operating the ventilation system following the supply process (see patent document 1).

Also, another decontamination process method for decontaminating a decontamination target having a complex shape is known, in which a cycle of a decompression process and a supply process and a pressure recovery process repeats. In the decompression process, a chamber containing a decontamination target is decompressed. In the supply process, a decontamination vapor is supplied to the chamber. In the pressure recovery process, the pressure inside the chamber, which was decompressed, is recovered (see patent document 2).

REFERENCE DOCUMENTS

[patent document 1] JP patent 4,380,411
[patent document 2] JP patent 5,163,882

By a decontamination process method, which is like the method disclosed in patent document 1 above, however, there are drawbacks. The decontamination vapor that is supplied into the chamber is likely to condense on a surface of the decontamination target. Since then, it has been difficult to cause the vapor to permeate inside the decontamination target even if the supply of the vapor repeats. In addition, in a case where the decontamination target has a complex shape that is a target to be decontaminated as discussed in patent document 2 above, it is difficult to completely decontaminate such a decontamination target.

In the decontamination process method of patent document 2, it is required to prepare a chamber that is capable of decompressing. Also, since outer air of the chamber may enter the chamber due to the decompression (or lower pressure state), the decontamination target is further polluted by microbe such as bacteria or virus that are present in the outer air.

Considering these drawbacks, the invention is to provide a decontamination process device and the method therefore which is capable to decontaminate a decontamination target having a complex shape, and to prevent microbe outside from entering the chamber during the decontamination process.

SUMMARY

A decontamination process device disclosed in the application includes a chamber that contains a decontamination target, a heating device that generates decontamination vapor, an air sending part that sends the decontamination vapor into the chamber, a ventilation system that ventilates the chamber; and a controller that controls operations of the decontamination process device, the controller performing a supply process that supplies a predetermined amount of the decontamination vapor into the chamber by activating the heating device and the air sending part, and an elimination process that eliminates a decontamination component in the chamber after the supply process by activating the ventilation system. Wherein the ventilation system is provided with a supply part and an exhaust part, and is configured to adjust an ventilation amount, which is a total air amount outgoing to and incoming from the chamber through the supply part or the exhaust part, and the controller is set to repeat the supply processes at multiple times, and to perform a dry process between the repeated supply processes, the dry process vaporizing a condensed liquid made from the decontamination vapor in the chamber by activating the ventilation system, and to maintain the chamber at a positive pressure during the dry process by adjusting the ventilation amount of the ventilation system.

A decontamination process method disclosed in the application including a supply process that supplies a predetermined amount of a decontamination vapor into a chamber in which a decontamination target is accommodated and an elimination process that eliminates a decontamination component, which is a target to be eliminated, remaining in the chamber after the supply process by ventilating the chamber includes repeating the supply process at multiple times, performing a dry process between two of the repeated supply processes, the dry process vaporizing a condensed liquid made from the decontamination vapor in the chamber by ventilating the chamber. The dry process continues for a shorter period than for the elimination process, and the chamber is maintained at a positive pressure during the dry process by adjusting a ventilation amount, which is a total air amount outgoing to and incoming from the chamber, for the ventilation.

According to some of the advantages of the invention, because the dry process is provided between the repeated supply processes for supplying the decontamination vapor into the chamber, condensed liquid from the decontamination vapor, which is generated inside the chamber, is to be vaporized during the dry process, making it possible to cause the decontamination vapor to permeate inside the decontamination target. Further because there is no decompression process, it becomes rare for microbe to enter the chamber from the outside.

BRIEF DESCRIPTION OF THE DRAWINGS

FIG. 2 illustrates a decontamination process method.

DETAILED DESCRIPTION OF THE PREFERRED EMBODIMENTS

Figure 1:
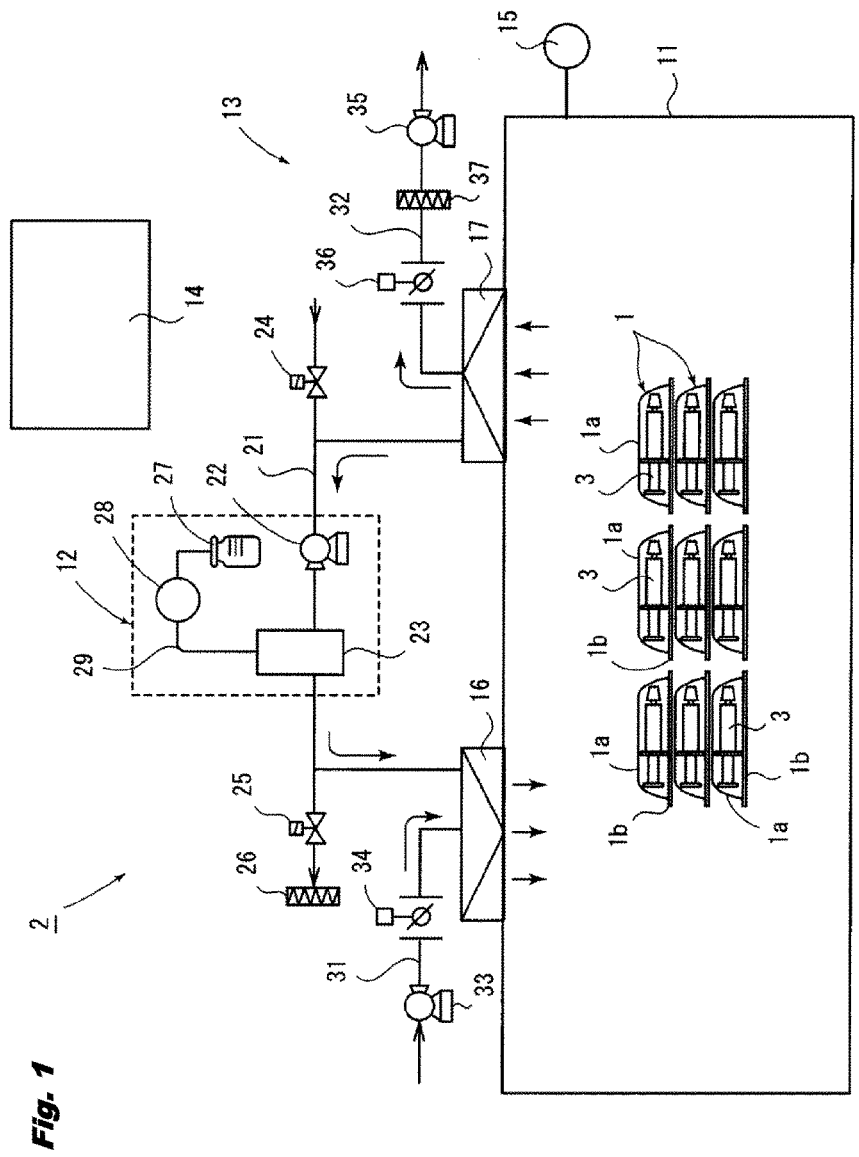
FIG. 1 illustrates structural view of a decontamination process device of the embodiment.

Hereinafter, embodiments are described. FIG. 1 illustrates a decontamination process device 2 that decontaminates a wrapping container 1, which is a decontamination target, by eliminating microbe such as bacteria or virus using hydrogen peroxide vapor as decontamination vapor.

The wrapping container 1 is composed with container bodies 1a, which are transparent and contain syringes 3, and covers 1b that cover openings of the container bodies 1a.

The container body 1a is made of a material through which microbe does not penetrate and that is, for example, polyethylene-telephthalate (PET). Since the container body 1a is transparent, the contained syringe 3 is visible from its outside.

The cover 1b is made of a material that prevents microbe from penetrating and allows vapor including the hydrogen peroxide vapor to penetrate. For such a material meeting these requirements, a sheet made of high density polyethylene is available. Specifically, "Tyvek" (Registered Trademark) of DuPont is known.

When the above discussed wrapping container 1 is decontaminately processed by the decontamination process device 2, the hydrogen peroxide vapor permeates into the inside of the wrapping container 1 through the cover 1b. A surface of the syringe 3 is to be decontaminated.

After that, even though the wrapping container 1 is moved to an environment where a decontamination process has not been performed, the cover 1b prevents microbe from entering. The inside of the wrapping container 1 maintains a bio-clean condition.

Since such a wrapping container 1 has been known, further explanations are omitted. The invention can be applied to the above wrapping container 1 that is the decontamination target, however can be applied to a large sized wrapping container that contains multiple syringes, or to a medical use hand piece that has a complex shape for the decontamination process.

The decontamination process device 2 is provided with a chamber 11 that contains multiple of the wrapping containers 1, a decontamination vapor supply part 12 that supplies a predetermined amount of hydrogen peroxide vapor to an inside of the chamber 11 and a ventilation system 13 that ventilates the chamber 11. All operations of those parts are controlled by a controller 14.

The chamber 11 is installed in a clean room, having a window (not shown) for carrying in/out the wrapping containers 1, a pressure sensor 15 for measuring an inner pressure of the chamber 11, and first and second filters 16 and 17 that are provided on a ceiling.

The inside of the chamber 11 is maintained with a positive pressure by the ventilation system 13, also is maintained air-tight by closing the window.

The first and second filters 16 and 17 are so called high-efficiency particulate air (HEPA) filters, and are connected to the decontamination vapor supply part 12 and the ventilation system 13. The first filter 16 is arranged at a supply side for the chamber 11. The second filter 17 is arranged at an exhaust side from the chamber 11.

The decontamination vapor supply part 12 is provided with a circulation path 21 of which an outflow side connects to the first filter 16 and an inflow side connects to the second filter 17, air sending part 22, which is fan or the like, that is disposed at the circulation path 21, and a vaporization part 23 as a heating device that vaporizes the hydrogen peroxide solution as a decontamination agent.

The air sending part 22 circulates air through the circulation path 21 in an anti-clockwise direction in the drawing view. The sent air is supplied to the chamber 11 from the first filter 16. The air inside the chamber 11 is sucked and sent back to the air sending part 22 through the second filter 17, completing the circulation of the air.

A bifurcation path is formed in the circulation path between the second filter 17 and the air sending part 22, and a first on-off valve 24, which is controlled by the controller 14, is provided therebetween. Also, between the vaporization part 23 and the first filter 16, another bifurcation path, a second on-off valve 25 controlled by the controller 14 and catalyst 26 are provided.

Due to opening the first on-off valve 24, outer air is taken into the circulation path. Due to opening the second on-off valve 25, a portion of the circulating air is emitted outside. Therewith, the controller 14 is capable of controlling a ventilation amount of the air.

To the vaporization part 23, a tank 27 that retains the hydrogen peroxide solution of a predetermined density and a liquid supply pump 28 that sends a predetermined amount of the hydrogen peroxide solution from the tank 27 are connected.

The air sent by the air sending part 22 passes through the inside the vaporization part 23. The hydrogen peroxide vapor of the predetermined amount that is vaporized at the vaporization part 23 is supplied to the chamber 11 by the air sending part 22.

At the tank 27, the hydrogen peroxide solution of 35 wt % is retained. The liquid supply pump 28 drops the hydrogen peroxide solution of a one time amount (or one time dose) as measuring the solution in the tank 27 with a measuring device (not shown).

When the solution is dropped to the vaporization part 23 from the liquid supply pump 28, the solution is immediately vaporized turning into the hydrogen peroxide vapor, the vapor being supplied to the inside of the chamber 11 by the air sending part 22.

The ventilation system 13 is provided with an air supply path 31 connected to a first filter 16 and an exhaust path 32 connected to a second filter 17. The ventilation system 13 ventilates the chamber 11 by supplying an outer air to the chamber 11 through the air supply path 31 and discharging the inner air of the chamber 11 through the exhaust path 32.

In the air supply path 31, an air supply blower 33 that supplies the outer air to the chamber 11 and a first adjustment valve 34 of which an opening degree is controlled by the controller 14 are provided. In the exhaust path 32, an exhaust blower 35 and a second adjustment valve 36 are provided. A catalyst 37 is provided between the exhaust blower 35 and the second adjustment valve 36.

The outer air that is supplied to the chamber 11 through the air supply path 31 is clarified (or filtered) by the first filter 16. The inner air of the chamber 11 is discharged from the exhaust path 32 through the second filter 17. During the discharging, the catalyst 37 dissolves the hydrogen peroxide components.

With the ventilation system 13 having these parts, by adjusting an air supply amount from the exhaust path 32 by the exhaust blower 35 and the first adjustment valve 34 and an exhaust amount from the exhaust path 32 by the exhaust blower 35 and the second adjustment valve 36, the ventilation amount is to be adjustable, causing the inner pressure of the chamber 11 to be variable.

Specifically, due to the control of the controller 14, by making the air supply amount from the air supply path 31 greater than the exhaust amount from the exhaust path 32, the inner pressure of the chamber 11 is to be positive (or greater than the outer pressure). On the other hand, by controlling the difference between the air supply and exhaust amounts, the inner pressure of the chamber 11 increases or decreases.

The air supply blower 33 and the exhaust blower 35 both have greater blow capacities than the air sending part 22 of the decontamination vapor supply part 12, is capable to ventilate with large air amount.

Hereinafter, with the disclosure of FIG. 2, a decontamination process method of the wrapping container 1 using the decontamination process device 2 is described. In FIG. 2, the vertical axis indicates an inner pressure (or gauge pressure) of the chamber 11 (Pa), the horizontal axis indicates time (or passage of time).

Before a decontamination process is performed, a plurality of the wrapping containers 1 are placed inside the chamber 11. The chamber 11 is sealed by the window so that the inside is air-tight. At the time, the covers 1b of the wrapping containers 1 are mounted such that the covers 1a are exposed in the chambers 11.

In the embodiment, similar to the conventional decontamination process method, a supply process in which a predetermined amount of hydrogen peroxide vapor is supplied to the chamber 11 and an elimination process in which the hydrogen peroxide components are eliminated by activating the ventilation system 13 are set by the controller 14. Further, in the embodiment, supply processes S1 and S3 are set in order to repeat the supply processes at multiple times. Dry process S2 for vaporizing condensed liquid of the decontamination vapor generated in the chamber is set between these first and second time supply processes S1 and S3, and another elimination process S4 is set after the second time supply process S3.

Regarding an explanation of the supply process S1, the supply process S1 is a process to supply a predetermined amount of the hydrogen peroxide vapor which corresponds for one time process (or a dose for one time process) to the chamber 11 and to decontaminate the wrapping containers 1 and the syringes 3 inside the wrapping containers 1.

The supply process S1 of the embodiment is, in further details, composed with processes that are an elevation temperature process S1a, a vaporization process S1b and a keeping process S1c. Among them, the elevation temperature process S1a is a process in which the vaporization part 23 and a portion of the circulation path 21 that is from the circulation path 21 to the chamber 11 are heated to raise their temperatures.

Namely, when performing the supply process S1, the vaporization part 23 and a tube section of the circulation path 21 may not be fully heated because the decontamination vapor supply part 12 has not been activated.

In order to prevent the hydrogen peroxide vapor from being condensed inside the tube section in the vaporization process S1b following to the elevation temperature process S1a, the tube section is to be heated in advance by the elevation temperature process S1a.

More specifically explained, the controller 14 activates the air sending part 22 to circulate air in the circulation path 21. When the blow amount by the air sending part 22 reaches a predetermined blow amount, the controller 14 activates the vaporization part 23 while stopping the liquid supply pump 28.

Thereby, without generating the hydrogen peroxide vapor at the vaporization part 23, only air that is supplied by the air sending part 22 is heated. As running through the circulation path 21, the heated air heats the tube section.

In the elevation temperature process S1a, the controller 14 opens the first on-off valve 24 that is disposed at the circulation path 21 and positioned at an upstream side from the air sending part 22. Thereby, the outer air is additionally supplied to the chamber 11.

As the result, the inside of the chamber 11 is gradually pressured by the supplied outer air. After that, when the pressure sensor 15 detects that the chamber 11 reaches a predetermined positive pressure, the controller 14 opens the second on-off valve 25 that is positioned at a downstream side from the vaporization part 23, and discharges a part of the air running through the circulation path 21, and maintains the inside of the chamber 11 at a predetermined positive pressure.

Additionally, in the elevation temperature process S1a, the air supply blower 33 and the exhaust blower 35 of the ventilation system 13 are not activated, only the air sending part 22 of the decontamination vapor supply part 12 is activated. Due to the operation of the air sending part 22, the inside of the chamber 11 is maintained at the positive pressure.

The elevation temperature process S1a continues until the temperature of the circulation path 21 reaches a predetermined temperature and the inside of the chamber 11 is controlled to a predetermined positive pressure. For example, it lasts for 20 minutes.

The vaporization process S1b of the supply process Si following the elevation temperature process S1a is a process that generates the hydrogen peroxide vapor by the decontamination vapor supply part 12, and supplies a predetermined amount of the hydrogen peroxide vapor to the chamber 11.

Specifically, the controller 14 causes the liquid supply pump 28 of the decontamination vapor supply part 12 to drop a predetermined amount of the hydrogen peroxide solution to the vaporization part 23 as measuring the solution, generating the predetermined amount of the hydrogen peroxide vapor. When the hydrogen peroxide vapor runs through the circulation path 21 and is supplied to the chamber 11, the inner pressure of the chamber 11 urgently rises.

However, if the hydrogen peroxide vapor is kept supplied to the chamber 11 until the chamber becomes a saturation state, the hydrogen peroxide vapor condenses on inner walls of the chamber 11 or surfaces of the wrapping containers 1, resulting in gradually decreasing the inner pressure of the chamber 11.

On the other hand, the controller 14 controls the air sending part 22 and the first and second on-off valves 24 and 25 of the circulation path 21 in correspondence with variations of the pressure as observing the pressure sensor 15 so that the chamber 11 is maintained at a positive pressure that is within a predetermined pressure range. Additionally, the hydrogen peroxide vapor discharged through the second on-off valve 25 is to be dissolved by the catalyst 26. The vaporization process S1b lasts, for example, for 16 minutes.

The keeping process S1c of the supply process Si following the vaporization process S1b is a process that maintains a status where the chamber 11 is filled with the hydrogen peroxide vapor.

Specifically, from the status of the vaporization process S1b, the controller 14 stops the liquid supply pump 28 and stops heating the vaporization part 23 to shut out the supply of the hydrogen peroxide vapor. On the other hand, the controller 14 continues the activation of the air sending part 22 to maintain the chamber 11 at the positive pressure by controlling the first and second on-off valves 24 and 25 of the circulation path 21.

During the process, the decontamination action of the hydrogen peroxide vapor supplied at the vaporization process S1b is fully performed.

The keeping process S1c continues, for example, for 30 minutes.

Additionally, when a fully decontamination result is obtained by supplying the decontamination vapor of one time dose at the end of the first supply process S1, it proceeds to an elimination process for eliminating decontamination components that are residuals of the hydrogen peroxide vapor.

However, in a case of decontaminating a decontamination target for which the decontamination action does not fully works, like the wrapping containers 1 of the embodiment, it is necessary to repeat the supply process at multiple times. In the embodiment, the first time supply process S1 and the second time supply process s3 are performed. Further, a dry process S2 is performed between the processes S1 and S3.

At the dry process S2, the ventilation system 13 is activated to ventilate the chamber 11 and to vaporize the condensed liquid attached to the inside of the chamber 11 or the surfaces of the wrapping containers.

The dry process S2 is composed with a low speed aeration process S2a, a high speed aeration process S2b and an elevation pressure process S2c.

Initially, at the elevation pressure process S2c, continued from the keeping process S1c of the supply process S1, the positive pressure control, which is performed by the air sending part 22 and the first and second on-off valves 24 and 25 of the decontamination vapor supply part 12, is maintained. At such a state, the air supply blower 33 of the air supply path 31 composing the ventilation system 13 is activated at a low speed operation. After that, by opening the first adjustment valve 34, the outer air is supplied to the chamber 11 through the air supply path 31.

When the air supply blower 33 reaches a predetermined blow amount as the low speed aeration, in addition to opening the second adjustment valve 36 of the exhaust path 32 composing the ventilation system 13, the exhaust blower 35 also is activated at a predetermined blow amount by the low speed operation as the low speed aeration, resulting in discharging the air in the chamber 11 to the outside.

The controller 14 maintains the chamber 11 at the positive pressure by the air supply amount from the air supply path 31 by the air supply blower 33 and the first adjustment valve 34 and the exhaust amount from the exhaust path 32 by the exhaust blower 35 and the second adjustment valve 36. When the exhaust is frequently performed in order to enhance the ventilation efficiency, the pressure inside the chamber 11 tends to decrease.

As discussed here, at the low speed aeration process S2a, operations of the air sending part 22 of the decontamination vapor supply part 12 and the air supply blower 33 and the exhaust blower 35 of the ventilation system 13 are overlapped. Thereby, the positive pressure of the chamber 11 is maintained for sure.

The low speed aeration process S2a continues, for example, for 10 minutes.

When the positive pressure of the chamber 11 is securely maintained by the low speed aeration process S2a, it proceeds to the high speed aeration process S2b.

At the high speed aeration process S2b, the controller 14 drives the air supply blower 33 and the exhaust blower 35 at high speed, performs massive ventilation with a larger blow amount than that of the low speed aeration process S2a, and maintains the positive pressure by adjusting the air supply amount and the exhaust amount. Further, the pressure inside the chamber slightly increases by the blow pressure.

The high speed aeration process S2b continues, for example, for 20 minutes.

As discussed above, at the dry process S2, the ventilation of the chamber 11 is performed using the air supply blower 33 and the exhaust blower 35 that have greater blow amounts than the air sending part 22 of the decontamination vapor supply part 12 has. Thereby, the condensed liquid is rapidly vaporized.

Additionally, for the ventilation at the dry process S2, it is enough as long as the condensed liquid attached to the inner surface of the chamber 11 and the surfaces of the syringes 3 or the like contained in the wrapping containers 1. Thereby, the ventilation period for the dry process S2 is set shorter than that for the elimination process S4 performed later.

The elevation pressure process S2c of the dry process S2 following the high speed aeration process S2b is a process that elevates the pressure of the chamber 11 for an elevation temperature process S3a of the supply process S3 that is next.

Specifically, when the high speed aeration process S2b is completed, the controller 14 controls the air supply blower 33 and the first adjustment valve 34 of the air supply path 31 to perform the air supply at the minimum blow amount from the air supply path 31, and, at the exhaust path 32, stops the exhaust blower 35 and shuts off the second adjustment valve 36 so that the exhaust is stopped.

Thereby, the exhaust stops but only the air supply is performed, resulting in pressuring the chamber 11. The elevation pressure process S2c continues until the chamber 11 reaches a predetermined positive pressure.

As discussed above, by setting the elevation pressure process S2c in the dry process S2, the blow amount of the air supply blower 33 is set close to the blow amount of the air sending part 22. Also, it proceeds in the supply process S3 after pressuring the chamber 11 to a predetermined pressure. Accordingly, an occurrence of the rapid pressure variations caused by switching the valves is avoidable.

When the dry process S2 is completed, the controller 14 performs a second time supply process S3. Similar to the first time supply process S1, the process is to decontaminate the wrapping containers 1 and the Syringes 3 inside the wrapping containers 1 by supplying the hydrogen peroxide vapor of a predetermined amount to the chamber 11.

The second time supply process S3, as well as the first time supply process S1, is composed with an elevation temperature process S3a, a vaporization process S3b and a keeping process S3c. Since each of the processes performs in the same fashion as the elevation temperature process S1a, the vaporization process S1b and the keeping process S1c, the details are omitted.

However, at the second time elevation temperature process S3a, the temperature of the circulation path 21 of the circulation path 21 has risen due to the done processes, it is possible to complete the elevation temperature process S3a for a shorter period than the first time elevation temperature process Sla. The elevation temperature process S3a is set to continue, for example, for 5 minutes.

The vaporization process S3b and the keeping process S3c following the elevation temperature process S3a are respectively set to continue, for example, for 16 minutes and 30 minutes in the same fashion as the vaporization process S1b and the keeping process S1c of the first time supply process S1.

Also, as shown in FIG. 2, at the vaporization process S3b of the second time supply process S3, the inner temperature of the chamber 11 is higher than at the first time. Therefore, the hydrogen peroxide vapor is not rapidly condensed, and the pressure is higher than at the first time, but decreases due to the occurrence of the condensation.

As the keeping process S3c, when the pressure sensor 15 detects a lower setting threshold of pressure, the controller 14 makes the first on-off valve 24 open and the second on-off valve 25 close, causing the chamber 11 to be pressured. After that, when the pressure elevates and an upper setting threshold is detected, the controller 14 makes the second on-off valve 25 open, causing the chamber 11 to be depressed.

As discussed in the embodiment, in addition to repeating the supply process S1 and the supply process S3 at multiple times, the dry process S2 is performed at a middle of the supply process Si and the supply process S3. Therewith, it is possible to complete more thorough decontamination process for a decontamination target that has a complex inner structure such as a syringe contained inside the supply process S1.

Namely, hydrogen peroxide vapor made by vaporizing hydrogen peroxide solution is able to contact the decontamination target in a vapor state. On contacting the target, the hydrogen peroxide component is condensed earlier than water, and acts at high density, resulting in highly decontaminative effect.

However, once the surface of the decontamination target becomes wet, the vaporization state cannot be maintained, and the condensation rapidly proceeds. the decontaminative effect reaches a saturation (or no further effect can be obtained after the saturation).

Especially, as shown in the embodiment, in a case where an inner structure of a decontamination target having a complex shape, such as the syringes 3 inside the wrapping containers 1, is to be decontaminated, there is a drawback that the hydrogen peroxide vapor cannot reach the inner structure.

Therefore, by setting the dry process S2 of the embodiment, condense liquids of the inside the chamber 11 or on the surface of the decontamination target are vaporized. By performing the second time supply process S3, the supply of the decontamination vapor is repeated, making it possible for the hydrogen peroxide vapor to reach the inner structure of the decontamination target.

An elimination process S4 following the supply process S3 is a process that eliminates the hydrogen peroxide components in the chamber 11 by ventilation by the ventilation system 13, composed with a low speed aeration process S4a, and a high speed aeration process S4b.

The low speed aeration process S4a performs the same operations as the low speed aeration process S2a at the dry process S2. The low speed aeration process S4a maintains the chamber 11 at a positive pressure and proceeds from the supply process S3 to S4 by the air sending part 22 of the decontamination vapor supply part 12 that operates as continued to the supply process S3 and the ventilation system 13 overlappingly operating.

The low speed aeration process S4a is set for 10 minute in the same fashion as the low speed aeration process S2a of the dry process S2.

At the high speed aeration process S4b after that, only the ventilation system 13 operates in the same fashion as the high speed aeration process S2b of the dry process S2.

In order to eliminate the hydrogen peroxide components in the chamber 11, the high speed aeration process S4b is set for 410 minutes that is adequately longer than the period for the dry process S2.

By performing the elimination process S4, the hydrogen peroxide components in the chamber 11 can be eliminated, also the hydrogen peroxide components that are attached to the inner structure of the syringe 3 contained in the wrapping container 1 or that permeate in the materials are vaporized and discharged.

Additionally, in the above embodiment, the dry process S2 and the second time supply process S3 are each performed one time. It is possible to repeat two sets of the above process in correspondence with a decontamination target that is a subject, and to perform the elimination process S4 at the end.

What is claimed is:

1. A decontamination process device, comprising:
    a chamber that contains a decontamination target;
    a circulation path that has a pair of ports at both ends thereof, the ports being connected to the chamber such that air outgoing from the chamber through one of the ports returns to the chamber through the other of the ports after passing through the circulation path wherein the one port from which the air outgoes is defined at an upstream side and the other port from which the air returns is defined at a downstream side in correspondence with an air flow direction in the circulation path;
    a vaporization part that generates decontamination vapor and is disposed in the circulation path;
    a first blower that sends the decontamination vapor into the chamber through the circulation path;
    a ventilation system that ventilates the chamber; and
    a controller that controls operations of the decontamination process device, the controller performing
        a supply process that supplies a predetermined amount of the decontamination vapor into the chamber by activating the vaporization part and the first blower, and
        an elimination process that eliminates a decontamination component in the chamber after the supply process by activating the ventilation system, wherein
    the ventilation system is provided with a supply part and an exhaust part, and is configured to adjust a ventilation amount, which is a total air amount outgoing to and incoming from the chamber through the supply part or the exhaust part,
    the circulation path is provided with a first on-off valve and a second on-off valve, the first on-off valve being positioned at the upstream side from the first blower and functioning to import outer air, which surrounds the decontamination process device, to the circulation path, and the second on-off valve being positioned at the downstream side from the first blower and functioning to export the air, which comes from the first blower through the circulation path, to the outer air, and
    the controller is set to repeat the supply processes at multiple times, to perform a dry process between the repeated supply processes, the dry process vaporizing a condensed liquid made from the decontamination vapor in the chamber by activating the ventilation system while the vaporization part does not generate the decontamination vapor, the dry process being completed in a shorter period than the elimination process is, and to maintain the chamber at a positive pressure during the dry process by adjusting the ventilation amount of the ventilation system controlling the first blower, the first on-off valve and the second on-off valve.

2. The decontamination process device of claim 1, wherein
the controller is set to perform an elevation pressure process in which a pressure inside the chamber is elevated while transiting from the dry process to the supply process.

3. The decontamination process device of claim 1, wherein
the supply part is composed with a supply blower that blows the outer air into the chamber,
the exhaust part is composed with an exhaust blower that blows the air in the chamber to the outer air,
during the supply processes, the chamber is maintained at the positive pressure by controlling the first blower, the first on-off valve and the second on-off valve, and
when the dry process starts after the supply processes, the supply blower is activated first and the exhaust blower is activated next to the supply processes, and the chamber is maintained at the positive pressure by adjusting the ventilation amount caused by the supply blower and the exhaust blower.

4. The decontamination process device of claim 3, wherein
the first blower, the first on-off valve and the second on-off valve are continued being controlled in the same manner as in the supply processes for a predetermined period after the supply blower and the exhaust blower are activated.

* * * * *